United States Patent
Groenendaal

(10) Patent No.: US 6,713,637 B2
(45) Date of Patent: Mar. 30, 2004

(54) PROCESS FOR PREPARING A 2-HYDROXYMETHYL-2,3-DIHYDRO-THIENO [3,4-B][1,4] DIOXINE-5,7-DICARBOXYLIC ACID DIESTER

(75) Inventor: Bert Groenendaal, Sinaai (BE)

(73) Assignee: Agfa-Gevaert (BE)

( * ) Notice: Subject to any disclaimer, the term of this patent is extended or adjusted under 35 U.S.C. 154(b) by 0 days.

(21) Appl. No.: 10/429,305

(22) Filed: May 5, 2003

(65) Prior Publication Data

US 2003/0216585 A1 Nov. 20, 2003

Related U.S. Application Data

(60) Provisional application No. 60/382,576, filed on May 22, 2002.

(30) Foreign Application Priority Data

May 14, 2002 (EP) .............................................. 02100490

(51) Int. Cl.$^7$ ............................................ C07D 495/02
(52) U.S. Cl. ....................................................... 549/50
(58) Field of Search ........................................... 549/50

(56) References Cited

U.S. PATENT DOCUMENTS

| 5,111,327 A | 5/1992 | Blohm et al. |
| 6,369,239 B2 * | 4/2002 | Rauchschwalbe et al. .... 549/50 |
| 6,528,662 B2 * | 3/2003 | Jonas .......................... 549/50 |

OTHER PUBLICATIONS

Search Report for EP 02 10 0490 (Oct. 16, 2002).

* cited by examiner

Primary Examiner—Deborah C Lambkin
(74) Attorney, Agent, or Firm—Leydig Voit & Mayer, Ltd.

(57) ABSTRACT

A process for preparing a 2-hydroxymethyl-2,3-dihydro-thieno[3,4-b][1,4]dioxine-5,7-dicarboxylic acid diester comprising the reaction of the alkali salt of 3,4-dihydroxythiophene-2,5-dicarboxylic acid diester and epihalohydrin in a molar ratio in the range of 1.01 to 1.4 in a polar solvent or mixture of polar solvents at a temperature between −20° C. to the boiling point of the polar solvent or polar solvent mixture.

5 Claims, No Drawings

PROCESS FOR PREPARING A 2-HYDROXYMETHYL-2,3-DIHYDRO-THIENO[3,4-B][1,4] DIOXINE-5,7-DICARBOXYLIC ACID DIESTER

The application claims the benefit of U.S. Provisional Application No. 60/382,576 filed May 22, 2002, which is herein incorporated by reference.

FIELD OF THE INVENTION

The present invention relates to a novel process for preparing a 2-hydroxymethyl-2,3-dihydro-thieno[3,4-b][1,4]dioxine-5,7-dicarboxylic acid diester.

BACKGROUND OF THE INVENTION

Polythiophenes have been studied extensively due to their interesting electrical and/or optical properties (see Handbook of Conducting Polymers, Eds. Skotheim, T. A.; Elsenbaumer, R. L.; Reynolds, J. R., Marcel Dekker, New York, 1998, 2nd edition). Within these classes of electroconductive polymers, poly(3,4-alkylenedioxythiophenes) have particularly useful electrical and/or optical properties. Poly(3,4-ethylenedioxythiophene) [PEDOT] in association with the polyanion poly(styrene sulphonic acid) [PSS] is one of the most commercially successful conductive polymers in the world. It is being used in a wide variety of applications as described by L. Groenendaal et al. in 2000 in Advanced Materials, volume 12, pages 481–494.

3,4-Ethylenedioxythiophene (EDOT) and its derivatives are important starting materials in the production of PEDOT. L. Groenendaal et al. in 2000 in Advanced Materials, volume 12, pages 481–494 discloses that (2,3-dihydro-thieno[3,4-b][1,4]dioxin-2-yl)-methanol [EDOT-CH$_2$OH]:

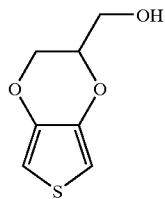

is an important intermediate in the synthesis of many new EDOT-derivatives e.g. to synthesise alkoxy-functionalized EDOT-derivatives (Chevrot et al. in 1998 in J. Chim. Phys., volume 95, pages 1258–1261), sulfonic acid-functionalized EDOT-derivatives (Chevrot et al. in 1998 in Journal Electroanalytical Chemistry, volume 443, pages 217–226, and in Synthetic Metals, volume 93, page 33) and oligoethyleneoxide-functionalized EDOT-derivatives (Roncali et al. in 2002 in Chemical Materials, volume 14, pages 449–457).

The synthesis of EDOT-CH$_2$OH was first described by Blohm et al. in U.S. Pat. No. 5,111,327. U.S. Pat. No. 5,111,327 discloses an electro-responsive polymer comprising chemically combined repeat units selected from the class consisting of,

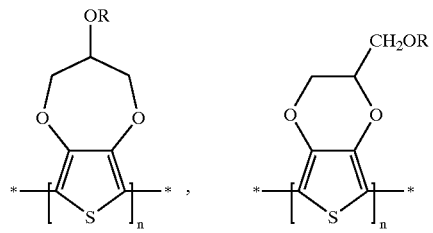

and a mixture thereof where R is a member selected from hydrogen or a C$_{(1-18)}$ organic radical.

A ca. 70/30 mixture of 2-hydroxymethyl-2,3-dihydro-thieno[3,4-b][1,4]dioxine-5,7-dicarboxylic acid dimethyl ester and 3-hydroxy-3,4-dihydro-2H-thieno[3,4-b][1,4]dioxepine-6,8-dicarboxylic acid dimethyl ester was produced using 3,4-dihydroxythiophene-2,5-dicarboxylic acid dimethyl ester and epibromohydrin. This mixture can in principle be separated by column chromatography, but this is extremely difficult if not impossible as reported by Ng et al. in 1997 in J. Mater. Sci. Lett., volume 16, pages 809–811. The diester of EDOT-CH$_2$OH can then be hydrolysed to the dicarboxylic acid derivative and finally decarboxylated to EDOT-CH$_2$OH.

This synthesis has been used by different groups (e.g. by Chevrot et al. in 1998 in Journal Electroanalytical Chemistry, volume 443, pages 217–226 and Synthetic Metals, volume 93, page 33; and by Ng et al. in 1997 in J. Mater. Sci. Lett. Volume 16, pages 809–811), who obtained the mixture of monomers and used it as such. In 1997 in Polymer Preprints, volume 38(2), page 320, Reynolds et al. reported the synthesis of acetyl-protected 2-hydroxymethyl-2,3-dihydro-thieno[3,4-b][1,4]dioxine-5,7-dicarboxylic acid dimethyl ester using a double Williamson reaction using the expensive acetyl-protected 2,3-dibromo-1-propanol. The reaction yield was very low (25%). More recently in 2000 in Electrochemical Communications, volume 2, pages 72–76, Roncali et al. reported the synthesis of the diester of EDOT-CH$_2$OH via the double Williamson reaction of 3,4-dihydroxythiophene-2,5-dicarboxylic acid dimethyl ester with 2,3-dibromo-1-propanol, although the reaction yield was also fairly low (40%).

Since EDOT-CH$_2$OH is an important intermediate in the synthesis of many modified EDOT-derivatives, it is important to optimize its synthesis. The most interesting approach from an economic standpoint is the synthesis of the diester of EDOT-CH$_2$OH via the epihalohydrin-route. However, this approach suffers from three main problems: the obtaining of two isomers which are difficult to separate, the necessary use of a large excess of the very poisonous (T+) epichlorohydrin (1.6 equivalents) and the very long reaction time (48 hours).

OBJECTS OF THE INVENTION

It is therefore an aspect of the present invention to provide a process for preparing a 2-hydroxymethyl-2,3-dihydro-thieno[3,4-b][1,4]dioxine-5,7-dicarboxylic acid diester in the substantial absence of 3-hydroxy-3,4-dihydro-2H-thieno[3,4-b][1,4]dioxepine-6,8-dicarboxylic acid diester.

Further aspects and advantages of the invention will become apparent from the description hereinafter.

SUMMARY OF THE INVENTION

It has been surprisingly found that a 2-hydroxymethyl-2,3-dihydro-thieno[3,4-b][1,4]dioxine-5,7-dicarboxylic acid diester can be exclusively produced using a smaller excess of epihalohydrin and a shorter reaction time by using polar solvents such as DMF, DMA, DMSO, NMP or mixtures of polar solvents such as DMF and DMSO, temperatures between −20° C. and the boiling point of the particular solvent or solvent mixture and quantities of epihalohydrin between 1.01 and 1.4 equivalents with respect to the molar quantity of the thiophene derivative.

Aspects of the present invention are realized by a process for preparing a 2-hydroxymethyl-2,3-dihydro-thieno[3,4-b][1,4]dioxine-5,7-dicarboxylic acid diester comprising the reaction of the alkali salt of 3,4-dihydroxythiophene-2,5-dicarboxylic acid diester and epihalohydrin in a molar ratio in the range of 1.01 to 1.4 in a polar solvent or mixture of polar solvent at a temperature between −20° C. to the boiling point of the polar solvent or polar solvent mixture.

Further advantages and embodiments of the present invention will become apparent from the following description.

DETAILED DESCRIPTION OF THE INVENTION

Definitions

The term alkyl means all variants possible for each number of carbon atoms in the alkyl group i.e. for three carbon atoms: n-propyl and isopropyl; for four carbon atoms: n-butyl, isobutyl and t-butyl; for five carbon atoms: n-pentyl, 1,1-dimethyl-propyl, 2,2-dimethylpropyl and 2-methyl-butyl etc.

A chiral compound is a compound containing a chiral centre. A chiral centre is an atom, e.g. a carbon atom, that is attached to four different groups. A compound containing a chiral centre is not superimposable upon its mirror image and will exhibit chirality, chirality being the handedness of an asymmetric molecule. Such compounds, if isolated in a pure state, will generally exhibit rotation of polarized light detectable with a polarimeter.

Process for Preparing a Compound Containing a 2-hydroxymethyl-2,3-dihydro-thieno[3,4-b][1,4]dioxine-5,7-dicarboxylic acid diester According to the present invention, a process is provided for preparing a 2-hydroxymethyl-2,3-dihydro-thieno[3,4-b][1,4]dioxine-5,7-dicarboxylic acid diester [diester of (2,3-dihydro-thieno[3,4-b][1,4]dioxin-2-yl)-methanol] comprising the reaction of the alkali salt of 3,4-dihydroxythiophene-2,5-dicarboxylic acid diester and epihalohydrin in a molar ratio in the range of 1.01 to 1.4 in a polar solvent or mixture of polar solvent at a temperature between −20° C. to the boiling point of the polar solvent or polar solvent mixture used.

According to a first aspect of the process, according to the present invention, the process is carried out at a temperature between 40° C. and 100° C.

According to a second aspect of the process, according to the present invention, the polar solvent is selected from the group consisting of DMF, DMA, DMSO and NMP or mixtures thereof.

According to a third aspect of the process, according to the present invention, the epihalohydrin is epibromohydrin.

According to a fourth aspect of the process, according to the present invention, the 3,4-dihydroxythiophene-2,5-dicarboxylic acid diester has ester groups selected from the group consisting of methyl, ethyl, n-propyl and n-butyl e.g. the dimethyl, diethyl, di-n-propyl, di-n-butyl (or a combination of these such as methylethyl) ester of 3,4-dihydroxythiophene-2,5-dicarboxylic acid.

The invention is illustrated hereinafter by way of comparative and invention examples. The percentages and ratios given in these examples are by weight unless otherwise indicated. All experiments were performed under inert conditions (nitrogen).

COMPARATIVE EXAMPLE 1

There was added 7.7 mL of epibromohydrin and 1.92 g of potassium carbonate dissolved in 100 mL of water to a refluxing mixture of 18.06 g of 3,4-dihydroxythiophene-2,5-dicarboxylic acid dimethyl ester and 350 mL of ethanol. After heating at reflux for one hour, an additional 5.34 mL of epibromohydrin was added. After heating at reflux for 15 hours, an additional 1.0 g of potassium carbonate and 3.0 mL of epibromohydrin were added. The mixture was heated at reflux for a total of 48 hours. The resulting reaction mixture was analyzed with GC-MS, which showed that it consisted of a mixture of 30% 3-hydroxy-3,4-dihydro-2H-thieno[3,4-b][1,4]dioxepine-6,8-dicarboxylic acid dimethyl ester (7-membered ring) and 70% of 2-hydroxymethyl-2,3-dihydro-thieno[3,4-b][1,4]dioxine-5,7-dicarboxylic acid dimethyl ester (6-membered ring), identical to what has been described by Blohm et al. in U.S. Pat. No. 5,111,327.

INVENTION EXAMPLE 1

To 10.4 g of 3,4-dihydroxythiophene-2,5-dicarboxylic acid dimethyl ester 20.0 mL of methanol and 16.5 mL of sodium methoxide (30 wt % solution in methanol) were added after which the mixture was stirred for 1 minute. Then 52 mL of N,N-dimethylformamide (DMF) and 2 mL of dimethyl sulphoxide were added and the reaction mixture was again stirred for 1 minute. Then 4.10 mL of epibromohydrin was added at room temperature. The temperature of the reaction mixture was brought to 75° C. and the methanol was distilled off. Subsequently, the temperature was raised to 100° C. and stirring was continued for 5 hours. Analysis by GC-MS showed that the reaction mixture only contained the diester of 2-hydroxymethyl-2,3-dihydro-thieno[3,4-b][1,4]dioxine-5,7-dicarboxylic acid.

INVENTION EXAMPLE 2

To 5.2 g of 3,4-dihydroxythiophene-2,5-dicarboxylic acid dimethyl ester 10.0 mL of methanol and 8.3 mL of sodium methoxide (30 wt % solution in methanol) were added after which the mixture was stirred for 1 minute. Then 26 mL of N,N-dimethylacetamide (DMA) was added and the reaction mixture was again stirred for 1 minute. Then 2.0 mL of epibromohydrin was added at room temperature. The temperature of the reaction mixture was brought to 75° C. and the methanol was distilled off. Subsequently, the temperature was raised to 100° C. and stirring was continued for 6 hours. Analysis by GC-MS showed that the reaction mixture only contained the diester of 2-hydroxymethyl-2,3-dihydro-thieno[3,4-b][1,4]dioxine-5,7-dicarboxylic acid.

INVENTION EXAMPLE 3

To 5.2 g of 3,4-dihydroxythiophene-2,5-dicarboxylic acid dimethyl ester 10.0 mL of methanol and 8.3 mL of sodium methoxide (30 wt % solution in methanol) were added after which the mixture was stirred for 1 minute. Then 24 mL of N-methylpyrrolidinone (NMP) was added and the reaction mixture was again stirred for 1 minute. Then 2.0 mL of epibromohydrin was added at room temperature. The temperature of the reaction mixture was brought to 75° C. and the methanol was distilled off. Subsequently, the temperature was raised to 100° C. and stirring was continued for 3 hours. Analysis by GC-MS showed that the reaction mixture only contained the diester of 2-hydroxymethyl-2,3-dihydro-thieno[3,4-b][1,4]dioxine-5,7-dicarboxylic acid.

The reaction mixture was poured into 150 mL of water and extracted 5 times with 50 mL of tert-butyl methyl ether (MTBE). The organic fractions were combined and the solvent was removed by vacuum distillation. This yielded pure product as a yellow solid.

INVENTION EXAMPLE 4

To 5.2 g of 3,4-dihydroxythiophene-2,5-dicarboxylic acid dimethyl ester 10.0 mL of methanol and 8.3 mL of sodium methoxide (30 wt % solution in methanol) were added after which the mixture was stirred for 1 minute. Then 23 mL of dimethyl sulphoxide (DMSO) was added and the reaction mixture was again stirred for 1 minute. Then 2.0 mL of epibromohydrin was added at room temperature. The temperature of the reaction mixture was brought to 60° C. and the methanol was distilled off within minutes. After 15 minutes at 60° C. the reaction mixture was cooled to RT. Analysis by GC-MS showed that the reaction mixture only contained the diester of 2-hydroxymethyl-2,3-dihydro-thieno[3,4-b][1,4]dioxine-5,7-dicarboxylic acid.

The present invention may include any feature or combination of features disclosed herein either implicitly or explicitly or any generalisation thereof irrespective of whether it relates to the presently claimed invention. In view of the foregoing description it will be evident to a person skilled in the art that various modifications may be made within the scope of the invention.

I claim:

1. A process for preparing a 2-hydroxymethyl-2,3-dihydro-thieno[3,4-b][1,4]dioxine-5,7-dicarboxylic acid diester comprising the reaction of the alkali salt of 3,4-dihydroxythiophene-2,5-dicarboxylic acid diester and epihalohydrin in a molar ratio in the range of 1.01 to 1.4 in a polar solvent or mixture of polar solvent at a temperature between −20° C. to the boiling point of the polar solvent or polar solvent mixture.

2. Process according to claim 1, wherein said process is carried out at a temperature between 45° C. and the boiling point of the polar solvent or polar solvent mixture used.

3. Process according to claim 1, wherein said polar solvent is selected from the group consisting of DMF, DMA, DMSO and NMP or mixtures thereof.

4. Process according to claim 1, wherein epihalohydrin is epibromohydrin.

5. Process according to claim 1, wherein said 3,4-dihydroxythiophene-2,5-dicarboxylic acid diester has ester groups selected from the group consisting of methyl, ethyl, n-propyl and n-butyl.

* * * * *